(12) United States Patent
Cheatham, II (10) Patent No.: US 9,775,768 B2
(45) Date of Patent: Oct. 3, 2017

(54) INTERACTIVE THERAPEUTIC MAT (71) Applicant: Keith Duane Cheatham, II, Girard, OH (US)

(72) Inventor: Keith Duane Cheatham, II, Girard, OH (US)

(73) Assignee: Keith Duane Cheatham, II, Girard, OH (US)

( * ) Notice: Subject to any disclaimer, the term of this patent is extended or adjusted under 35 U.S.C. 154(b) by 1073 days.

(21) Appl. No.: 13/908,029

(22) Filed: Jun. 3, 2013

(65) Prior Publication Data

US 2013/0296745 A1  Nov. 7, 2013

Related U.S. Application Data (63) Continuation-in-part of application No. 12/693,764, filed on Jan. 26, 2010, now abandoned.

(Continued)

(51) Int. Cl.
*B60L 1/02* (2006.01)
*A61H 23/00* (2006.01)
(Continued)

(52) U.S. Cl.
CPC ............. *A61H 23/00* (2013.01); *A61F 7/007* (2013.01); *A61H 7/001* (2013.01); *A61H 23/02* (2013.01); *B60L 1/003* (2013.01); *A61F 7/08* (2013.01); *A61F 2007/0024* (2013.01); *A61F 2007/0079* (2013.01); *A61H 2201/0134* (2013.01);

(Continued)

(58) Field of Classification Search
CPC .. A61F 7/007; A61F 7/001; A61F 7/08; A61F 2007/007; A61F 2007/0024; A61F 2007/0138; A61F 2007/0079; A61H 23/02; A61H 2205/12; A61H 2205/081; A61H 2205/086; A61H 2201/0207; A61H 2201/1284; A61H 2201/5082; A61H 2201/0134; A61H 2201/0228; A61H 2201/5048; A61H 2201/5058; A61H 2201/5097; A61H 2201/0188; A61H 2201/5079; A61H 2201/5084; A61H 23/00; B60L 1/003; B60N 3/04; B60N 3/042; B60N 3/044; B60N 3/046; B60N 3/048; B60Q 3/007; B60Q 3/0283
See application file for complete search history.

(56) References Cited

U.S. PATENT DOCUMENTS

2,476,921 A   7/1949   Shock
2,820,454 A   1/1958   Wright
(Continued)

*Primary Examiner* — Shawntina Fuqua
(74) *Attorney, Agent, or Firm* — Mark E. Bandy; Rankin, Hill & Clark LLP (57) ABSTRACT

A therapeutic mat is described. The mat provides therapeutic relief in the form of vibratory motion and/or heat. The mat or pad is particularly useful as a floor mat in a vehicle. The mat includes provisions to enable powering the mat from a 12-volt direct current source, such as used in an automobile or other vehicle. A massage module can be removed from the mat to facilitate cleaning of the mat. The mat may also include one or more upwardly extending provisions for massaging the arch region of a user's feet. Also described are illuminated mats. The lights of a mat can operate based upon the operation of another mat, pulsations of the massage module, or based upon acoustic levels in the vehicle.

18 Claims, 6 Drawing Sheets

Related U.S. Application Data (60) Provisional application No. 61/147,155, filed on Jan. 26, 2009.

(51) Int. Cl.
    *A61H 7/00*         (2006.01)
    *A61H 23/02*       (2006.01)
    *A61F 7/00*         (2006.01)
    *B60L 1/00*        (2006.01)
    *A61F 7/08*         (2006.01)

(52) U.S. Cl.
    CPC ........ *A61H 2201/0138* (2013.01); *A61H 2201/0188* (2013.01); *A61H 2201/0207* (2013.01); *A61H 2201/0228* (2013.01); *A61H 2201/1284* (2013.01); *A61H 2201/5048* (2013.01); *A61H 2201/5058* (2013.01); *A61H 2201/5079* (2013.01); *A61H 2201/5082* (2013.01); *A61H 2201/5084* (2013.01); *A61H 2201/5097* (2013.01); *A61H 2205/081* (2013.01); *A61H 2205/086* (2013.01); *A61H 2205/12* (2013.01)

(56) References Cited

U.S. PATENT DOCUMENTS

| | | |
|---|---|---|
| 3,100,483 A | 8/1963 | Altmeyer et al. |
| 4,173,216 A | 11/1979 | Nolet |
| 4,326,506 A | 4/1982 | Kawabata |
| 4,329,981 A | 5/1982 | Dungl |
| 4,773,155 A | 9/1988 | Buchien |
| 4,979,502 A | 12/1990 | Hunt |
| 5,254,384 A | 10/1993 | Gordon |
| 5,490,821 A | 2/1996 | Wu |
| 5,628,079 A | 5/1997 | Kizemchuk et al. |
| 6,189,487 B1 | 2/2001 | Owen et al. |
| 6,481,877 B1 * | 11/2002 | Bello, Jr. ............... B60N 3/042 362/153 |
| 6,485,081 B1 | 11/2002 | Bingle et al. |
| 6,579,250 B2 | 6/2003 | Robbins, III et al. |
| 6,580,060 B1 | 6/2003 | Inman et al. |
| 6,736,442 B2 | 5/2004 | Gebreselassie et al. |
| 7,297,126 B2 | 11/2007 | Kries |
| 7,436,325 B2 * | 10/2008 | Bailey ................. B60N 3/04 341/176 |
| 7,629,896 B2 | 12/2009 | Blum et al. |
| 8,106,796 B2 | 1/2012 | Bailey |
| 2010/0130808 A1 | 5/2010 | Hattori |

\* cited by examiner

INTERACTIVE THERAPEUTIC MAT

CROSS REFERENCES TO RELATED APPLICATIONS

This application is a continuation-in-part application from, and claims priority upon, U.S. application Ser. No. 12/693,764 filed Jan. 26, 2010, which claims priority upon U.S. application Ser. No. 61/147,155 filed Jan. 26, 2009.

FIELD

The present subject matter relates to a therapeutic mat. The mat or pad may be in various forms such as a floor mat, a seat bottom, and a seat back. The mat or pad provides therapeutic relief in the form of vibratory motion and/or heat. In certain embodiments, the subject matter relates to vehicle floor mats which include lights and massage modules.

BACKGROUND

A wide variety of mats are known in the art. Many mats include vibrating elements for massaging and/or heating elements. Although such mats may be useful, problems arise if the mat requires cleaning or is otherwise immersed in liquid. Prolonged exposure to liquids such as cleaning water can damage electronic components and particularly, sensitive circuitry and vibrating components incorporated in the mat.

Massaging mats are typically provided with a large number of outwardly extending projections or "fingers". When a user presses against such mats, the "fingers" provide increased pressure at their points of contact with the user, thereby providing a pleasant feeling to the user. Although satisfactory in many regards, these mats typically have limited application since the projections are unable to reach certain regions of a user such as arches along the underside of a user's feet.

In view of the foregoing, a need exists for a therapeutic mat which can be easily cleaned and/or immersed in a cleaning liquid without the potential for damage. In addition, a need exists for an improved therapeutic mat which provides increased therapeutic benefits.

Illuminated automotive floor mats are also known in the art. Such mats provide lighting for floor regions of a vehicle. Although satisfactory in certain functional aspects, needs for mats having additional functions and features still exist.

SUMMARY

In one aspect, the present subject matter provides a vehicle floor mat. The mat comprises a thin, planar, flexible member defining an upwardly directed first face, an oppositely directed second face, and an interior hollow region between at least a portion of the first face and the second face. The flexible member is sized and shaped to reside along the floor of a vehicle cabin. The mat also comprises a massage module removably disposed in the interior hollow region of the flexible member. The massage module emits vibratory motion upon application of electrical power to the massage module. The mat also comprises at least one illuminating element affixed to the flexible member and visible along the first face of the flexible member upon application of electrical power to the illuminating element. The mat additionally comprises control provisions associated with the mat. The control provisions are configured to control the operation of the massage module and the at least one illuminating element, such that the operation of the illuminating element is dependent upon and follows the operation of the massage module.

In another aspect, the present subject matter provides a vehicle floor mat. The mat comprises a thin, planar, flexible member defining an upwardly directed first face, an oppositely directed second face, and an interior hollow region between at least a portion of the first face and the second face. The flexible member is sized and shaped to reside along the floor of a vehicle cabin. The mat also comprises a massage module removably disposed in the interior hollow region of the flexible member. The module emits vibratory motion upon application of electrical power to the massage module. The mat also comprises at least one illuminating element affixed to the flexible member and visible along the first face of the flexible member upon application of electrical power to the illuminating element. The mat also comprises an acoustic sensor and control provisions incorporated in the mat and configured to provide a control output signal based upon acoustic parameters sensed by the acoustic sensor. The control provisions are also configured to control the operation of the at least one illuminating element based at least in part upon the control output signal, such that the operation of the illuminating element is dependent upon and follows the acoustic parameters in the vehicle.

In yet another aspect, the present subject matter provides a plurality of vehicle floor mats comprising a primary vehicle floor mat including (i) at least one illuminating element, (ii) at least one vibratory component, and (iii) control provisions for controlling operation of the at least one illuminating element and the at least one vibratory component. The plurality of floor mats also comprise at least one secondary vehicle floor mat. Each secondary vehicle floor mat comprises (i) at least one illuminating element, and (ii) at least one vibratory component, wherein operation of the at least one illuminating element of the secondary vehicle floor mat and the at least one vibratory component of the secondary vehicle floor mat are controlled by the control provisions of the primary vehicle floor mat.

As will be realized, the subject matter is capable of other and different embodiments and its several details are capable of modifications in various respects, all without departing from the subject matter. Accordingly, the drawings and description are to be regarded as illustrative and not restrictive.

DETAILED DESCRIPTION OF THE EMBODIMENTS

The present subject matter relates to a therapeutic mat or pad which provides therapeutic relief in the form of vibratory massage and optionally, in combination with the emission of heat. The therapeutic mat or pad can be provided in several different forms, for example as a mat adapted for placement of a user's foot or feet thereon, or as a component of a seating unit, such as for example as a seat bottom or seat back. Preferably, the therapeutic mat or pad is adapted for use in a vehicle cabin, such as within the interior of an automobile or like vehicle, and so includes provisions for powering the therapeutic mat from the power system of the vehicle. These aspects and others are detailed herein.

The difficulties and drawbacks associated with previously known mats are overcome in the present apparatus for a therapeutic mat having a massage module that can be selectively removed from the mat. In certain aspects, the mat also includes one or more outwardly projecting members that transmit vibratory motion to the user.

In one embodiment, the present subject matter provides a vehicle floor mat comprising a thin, planar, flexible member defining an upwardly directed first face, an oppositely directed second face, and an interior hollow region between at least a portion of the first face and the second face. The first face defines at least one raised region. The flexible member is sized and shaped to reside along the floor of a vehicle cabin. The mat also comprises a massage module disposed in the interior hollow region of the flexible member. The module emits vibratory motion upon application of electrical power to the module. The mat further comprises a control unit for controlling the operation of the massage module. And, the mat additionally comprises an electrically conductive cord extending between the massage module and the control unit. The massage module includes at least one outwardly extending member that directs vibratory motion to the at least one raised region of the first face of the flexible member.

In another embodiment, the subject matter provides an electrically powered therapeutic mat comprising a thin, planar, flexible member defining a first upwardly directed face and a second oppositely directed face. The flexible member further defines a hollow interior region between at least a portion of the first face and at least a portion of the second face. The flexible member includes an assembly providing selective access to the interior region from one or both of the faces. The flexible member further includes at least one upwardly extending projection along the first face of the flexible member. The mat also comprises a massage module disposed in the interior region defined in the flexible member. The mat additionally comprises a heating element disposed in at least a portion of the flexible member. And, the mat comprises a control unit in communication with both the massage module and the heating element and configured for controlling the operation of each of the massage module and the heating element.

In yet another embodiment, the subject matter provides a mat adapted for placement on a vehicle seat. The mat comprises a thin, planar, flexible member sized and shaped to conform and be positioned on a vehicle seat. The flexible member defines a seat portion for placement on a seat cushion of the vehicle seat and a back portion for placement on a back cushion of the vehicle seat. The member defines a selectively accessible interior hollow region in at least one of the seat portion and the back portion of the flexible member. The mat further comprises at least one massage module disposed in the at least one interior hollow region defined in the flexible member. The module emits vibratory motion upon application of electrical power to the module. The mat also comprises a control unit for controlling the operation of the at least one massage module. And, the mat further comprises an electrically conductive cord extending between the control unit and the at least one massage module.

In yet additional embodiments, the subject matter provides a mat adapted for use as a vehicle floor mat. The mat can include a variety of components and features as described herein, but typically includes one or more lights in combination with a massage module. Electronic controls and associated power operating circuits are incorporated in the mat to operate and control operation of the lights and the massage module. Generally, the lights are configured to flash or change in intensity or color, i.e., wavelength of emission, based upon changes in vibrations of the massage module or from changing acoustic levels in the vehicle. Thus, for example, if the massage module is set to operate in a pulsating mode, the lights then also operate in a pulsating mode. Alternatively, the lights can be set to change in intensity and/or color based upon music or other noises in the vehicle.

In still another embodiment, mats featuring lights can also be configured so that collections of such mats can operate in unison based upon controls from a primary mat. For example, a family of lighted mats may be set to flash or change in light intensity or color based upon an acoustic sensor and controls in a primary mat. Other modes of operation of the family of mats are contemplated such as having the lights and/or massage modules of mats operate based upon the operation of a massage module in the primary mat or based upon noise levels in the vehicle sensed by the primary mat. Communication between mats in a family of mats can be wireless or alternatively, can use electrical cable connections.

Figure 1:
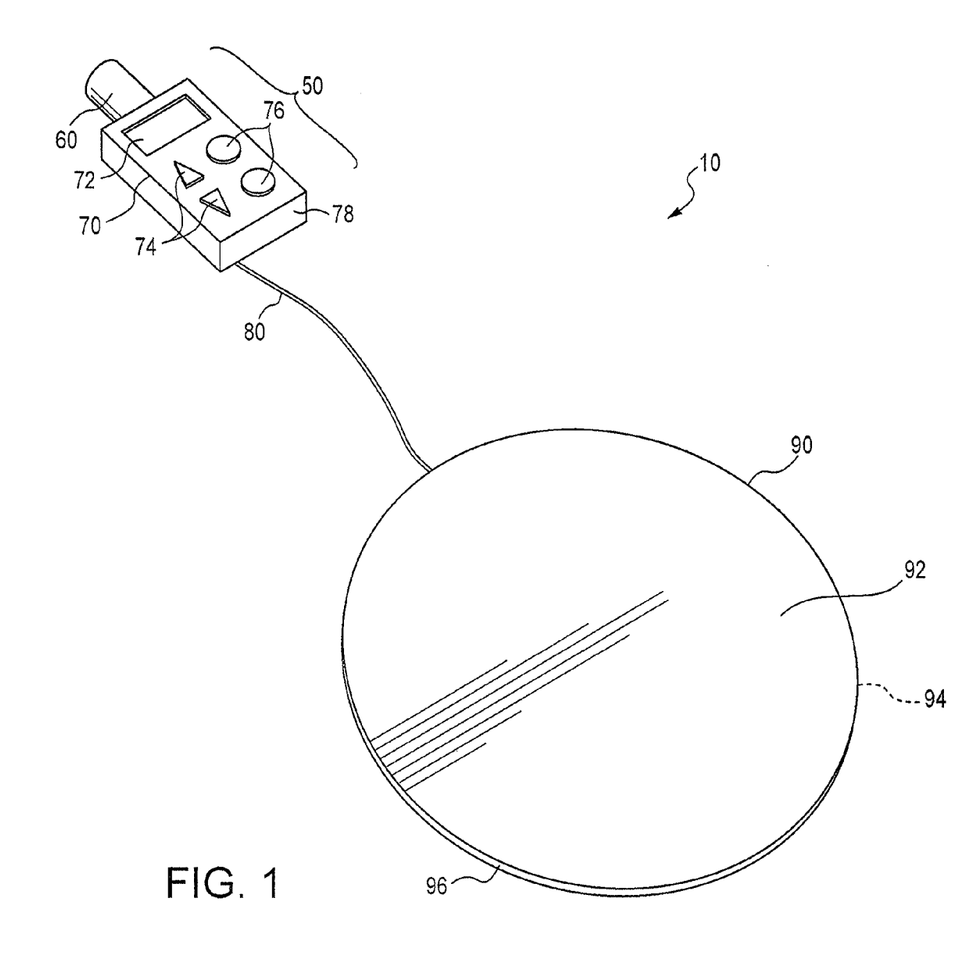
FIG. 1 is a schematic view illustrating a massage system used in various preferred embodiment mats or pads according to the present subject matter.

FIG. 1 is a schematic illustration of a massage system 10 used in a preferred embodiment therapeutic mat or pad, examples of which are described herein. The massage system 10 comprises a control and/or power unit 50 which includes a power plug 60 and/or adaptor module and a control unit 70. The control/power unit 50 is preferably in the form of a conventional 12-volt direct current (VDC) plug or adapter. The control unit 70 may be provided with an array of features including for example, but not limited to, an indicator 72, one or more control elements 74, one or more on/off elements 76, and a housing 78. The control unit 70 preferably is a microprocessor-based electronic unit which governs operation of one or more components used in the massage system 10 and/or the therapeutic mat for example. The indicator 72 provides information to the user such as the status of the device(s), desired temperature (in the event that heating elements are provided), actual temperature, operation levels, status codes, etc. It will be appreciated that the control unit 70 is not limited to these features.

The massage system 10 also includes a massage module 90 which may be in a variety of different forms, shapes, and configurations. A preferred form for the massage module 90 used in the system 10 is a relatively flat, planar, flexible member. The module 90 may also be in a variety of different shapes such as circular, oval, square, rectangular, polygonal, . . . etc. The module 90 is depicted in a circular shape in the accompanying figures. The module 90 defines a first face 92, an oppositely directed second face 94, and an edge 96 extending between the faces 92 and 94 and generally defining the outer perimeter of the module 90.

The massage system 10 further includes a power and/or communication cord 80 extending between the control/power unit 50 and the massage module 90. The cord 80 preferably is a multi-conductor cord and is adapted to provide electrical power to one or more powered devices utilized in the therapeutic mat or pad, such as the massage module 90, and/or one or more electrical heating elements. The cord 80 may also include one or more electrical conductors for providing or receiving electrical control signals used in the operation of the massage module 90 and/or heating elements. For example, temperature sensors may be provided in the mat which can provide electrical signals to the control unit 70 for governing the operation of the mat. It is also preferred that the power cord include appropriate insulation and in certain applications, a protective sheathing along its length.

It is also contemplated that one or more connectors can be provided in conjunction with the cord 80 to provide selectable connection and removal of either or both of the control/power unit 50 and the massage module 90 from the cord 80.

Figure 2:
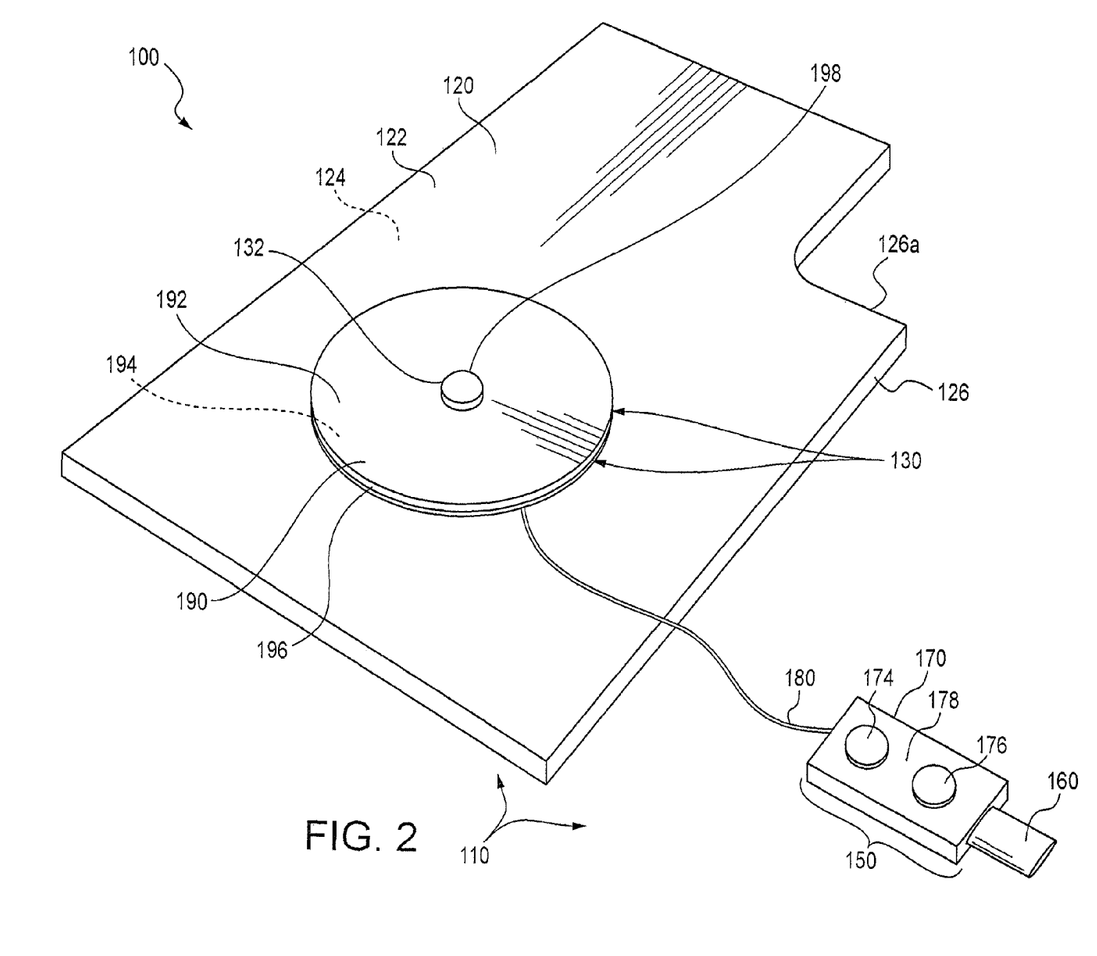
FIG. 2 is a schematic view of a preferred embodiment massaging foot mat in accordance with the present subject matter.

FIG. 2 is a schematic illustration of a preferred embodiment massaging foot mat 100 in accordance with the present subject matter. The mat 100 comprises a massage system 110. The massage system 110 generally corresponds to the previously described massage system 10. In this regard, it will be appreciated that the previous description for components of the system 10 applies to components of the system 110 having like numbering.

The massage system 110 includes a control/power unit 150 which preferably comprises a 12 VDC plug/adapter 160, and a control unit 170. The adapter or plug is preferably a male plug adapted to be inserted within and engage a female connector such as a vehicle cigarette lighter receptacle. The control unit may include one or more control elements 174, one or more on/off elements 176, and a housing 178. Although not specifically depicted, it will be understood that the control unit 170 may also include one or more indicator(s) for presenting information to the user.

The massage system 110 of the massaging foot mat 100 also preferably comprises a power/communication cord 180 extending from the control/power unit 150.

The massage system 110 of the massaging foot mat 100 also comprises one or more massage modules 190. In the version depicted in FIG. 2, the mat includes a single massage module 190. The one or more massage modules are preferably incorporated within a hollow interior region of the mat. As explained in greater detail herein, the massage module is preferably inserted in the hollow interior of the mat through one or more closure assemblies along a face of the mat. For example, a zippered opening could be provided on either a top or bottom face of the mat. The massage module could be accessed through the zippered opening. The module 190 defines an upwardly directed first face 192, an oppositely directed second face 194, and an edge 196 extending between the faces 192 and 194 and generally defining the outer periphery of the module 190. Preferably, the massage module 190 further includes one or more outwardly projecting members or "bumps" 198 for providing therapeutic massage action and in particular to select regions of a user's feet. In the embodiment depicted in FIG. 2, a single upwardly projection 198 is provided for reaching the arch region of a user's foot. It will be appreciated that the present subject matter is in no way limited to the particular configuration depicted in FIG. 2.

A human foot is characterized as having a transverse arch extending in a width direction along an underside of the foot, and a longitudinal arch extending in a length direction also along the underside of the foot. These concave regions along the underside of the foot are generally not accessible by flat massaging surfaces, or even planar surfaces with massaging "fingers" as known in the art. Provision of the outwardly projecting region or member 198 of the massage module 190 enables these regions of a user's feet to be contacted with and receive therapeutic massaging relief. Accordingly, the preferred embodiment mat includes one or two outwardly projecting members such as member 198, each of which is sized, shaped, and configured to reach and contact the concave arch regions along the underside of a human foot.

The massaging foot mat 100 also includes a mat 120. The mat is preferably in the form of a relatively thin, planar, flexible member adapted to reside along the floor, and particularly along the floor of an automotive or vehicle cabin. The mat may be formed from a wide array of materials and can utilize a single or multilayer construction. The mat defines an upwardly directed first face 122, an oppositely directed second face 124, and an edge 126 extending between the faces 122 and 124. For applications in which the massaging floor mat 100 is provided as a vehicle floor mat, the mat 120 can be in a shape corresponding to the shape of the floor region to receive the mat, and/or to accept components within the vehicle interior such as a gas pedal. The foot mat 100 is illustrated in FIG. 2 as featuring an inset edge region 126a, such as for accommodating a gas pedal when the foot mat 100 is used on the driver's side within a vehicle cabin.

A significant and preferred feature of the massaging foot mat 100 is a massage module access and retention system 130. The retention system releasably retains the one or more massage modules 190 in association with the mat 120. It will be appreciated that the mat 100 includes the massage module 190 within the interior of the mat, and thus the module 190 would not be visible from the mat exterior. FIG. 2 is schematic in nature and illustrates the module 190 for ease in understanding the subject matter. As explained herein, the module 190 is accessible and can be removed from or re-introduced into the mat 100 through one or more access and retention provisions provided along a region of the mat. The module access and retention system 130 can be provided in a wide variety of different configurations. One preferred configuration is depicted in FIG. 2, in which a pocket or other recessed region is defined in the mat 120 and preferably along the upwardly directed face 122 of the mat. The pocket or recessed region is sized and shaped to receive and accommodate the one or more massage modules 190. The module access and retention system 130 also preferably includes provisions for selectively accessing and/or retaining the module(s) 190 in the pocket or recessed region. An example of such provisions is a zipper extending entirely or partially along an edge region of the pocket. Upon appropriate placement and positioning of the massage module(s) in the pocket, the zipper can be closed to thereby conveniently enclose and retain the massage module(s) 190 in the mat 120. Other access and retention systems are contemplated such as for example, buttons, Velcro or hook and loop fasteners, and adhesive systems.

The mat 120 may optionally also be provided with one or more apertures through which the previously described therapeutic projection(s) 198 may extend. Thus, the projection(s) 198 may directly contact the underside of a user's foot. It will be understood that the aperture(s) are sized, shaped, and located corresponding to the size, shape, and location(s) of the therapeutic projection(s).

As previously noted, in one embodiment, the one or more projections 198 can be included with or extend from the massage module 190. In this version of the subject matter, provisions are included in the mat 120 to accommodate the projections 198, such as apertures or other structures in the mat which cooperate with the projections so that the projections can transmit vibratory motion directly from the module 190 to a user in contact with the projections. Alternatively, the subject matter includes forming or providing the one or more projections 198 as part of the mat 120 and locating such projections so that vibratory motion from the module 190 can be effectively transmitted thereto.

Figure 3:
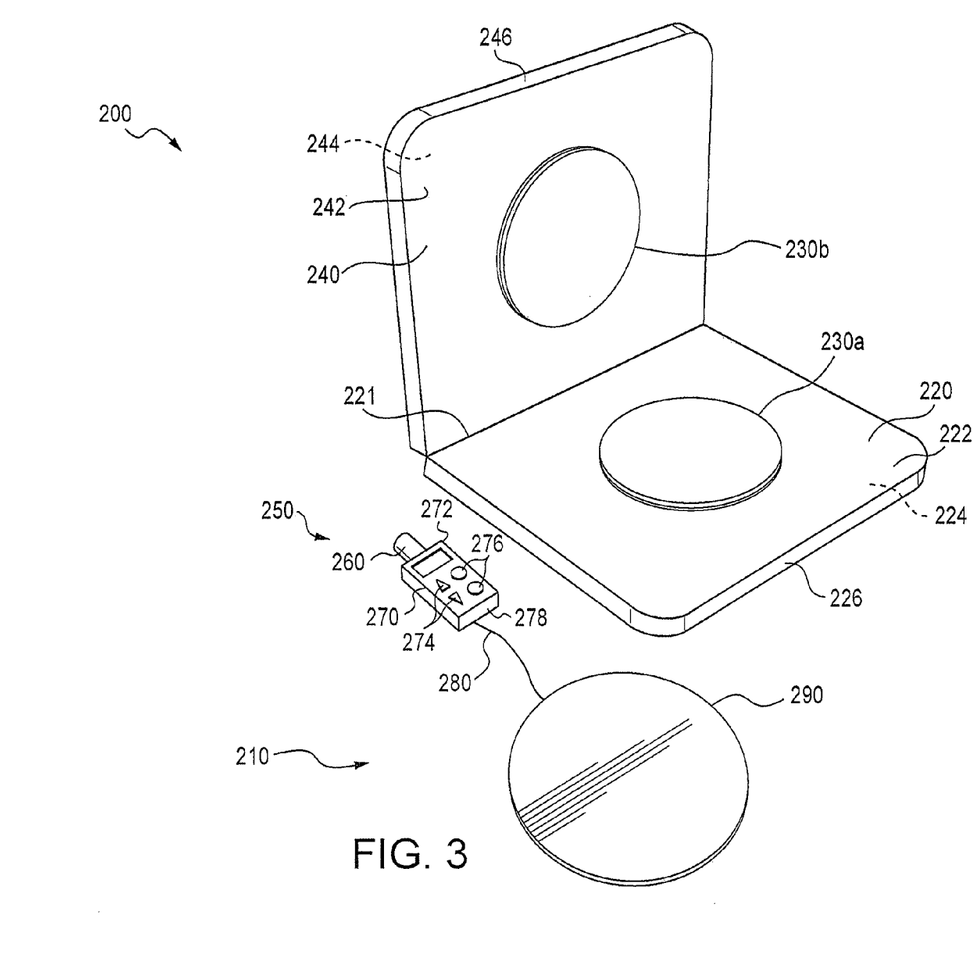
FIG. 3 is a schematic view of a preferred embodiment massaging seat bottom and seat back in accordance with the present subject matter.

FIG. 3 schematically depicts yet another embodiment according to the present subject matter. In this version of the present subject matter, a massaging seat system 200 is provided. The system 200 comprises a massage system 210, similar or identical to the previously described massage systems 10, 110. As previously noted, respective components of the massage system 210 correspond to components of the systems 10, 110 having like reference numbers. Generally, the massage system 210 includes a control/power unit 250 having a 12 VDC plug/adapter 260 and a control unit 270. The control unit 270 includes an indicator 272, one or more control elements 274, one or more on/off elements 276, and a housing 278. The massage system 210 also includes one or more massage modules 290, and a power/communication cord 280 extending between the control unit 270 and the massage module(s) 290.

The massaging seat system 200 further comprises one or more components of a seat, preferably a seat adapted to be used in a vehicle or the like, such as for example a seat bottom 220 and/or a seat back 240. It will be appreciated that the seat system 200 may comprise both a seat bottom 220 and a seat back 240; a seat bottom 220 by itself; or a seat back 240 by itself. Furthermore, it will be appreciated that for a version of the massaging seat system 200 in which both a seat bottom 220 and a seat back 240 are provided, the bottom and back may be formed such that they are permanently attached or releasably attached to one another such as along region 221.

Furthermore, in accordance with the present subject matter, it is contemplated that the seat bottom 220 and/or the seat back 240 may be formed as integral components of a seat assembly, such as for example, an automotive seat assembly. Alternatively, the seat bottom 220 and seat back 240 may be provided as auxiliary, add-on components which may be permanently or temporarily attached to the appropriate faces of a seating assembly.

Referring further to FIG. 3, the seat bottom 220 defines an upwardly directed first face 222, an oppositely directed second face 224, and an edge 226 extending therebetween. Similarly, the seat back 240 defines a frontwardly directed first face 242 an oppositely directed second face 244, and an edge 246 extending therebetween.

Preferably, both the seat bottom 220 and the seat back 240 include provisions for retaining one or more massage module(s) 290. These provisions may in many instances, be the same or similar as the access and retention provisions 130 described and shown in FIG. 2. Thus, for example the seat bottom 220 preferably includes a massage module retention system 230a; and the seat back 240 preferably includes a massage module retention system 230b. Preferably, each of these systems 230a and 230b are in the form of a pocket or recessed region in the respective seat bottom 220 and/or seat back 240 having a zippered region for releasably retaining one or more massage module(s) 290 positioned within the pocket or recessed region. Again, it will be understood that FIG. 3 is in schematic form showing the modules 230a and 230b. In reality, the modules would not be visible since they are retained within the interior of the seat bottom and back 220, 240.

Figure 4:
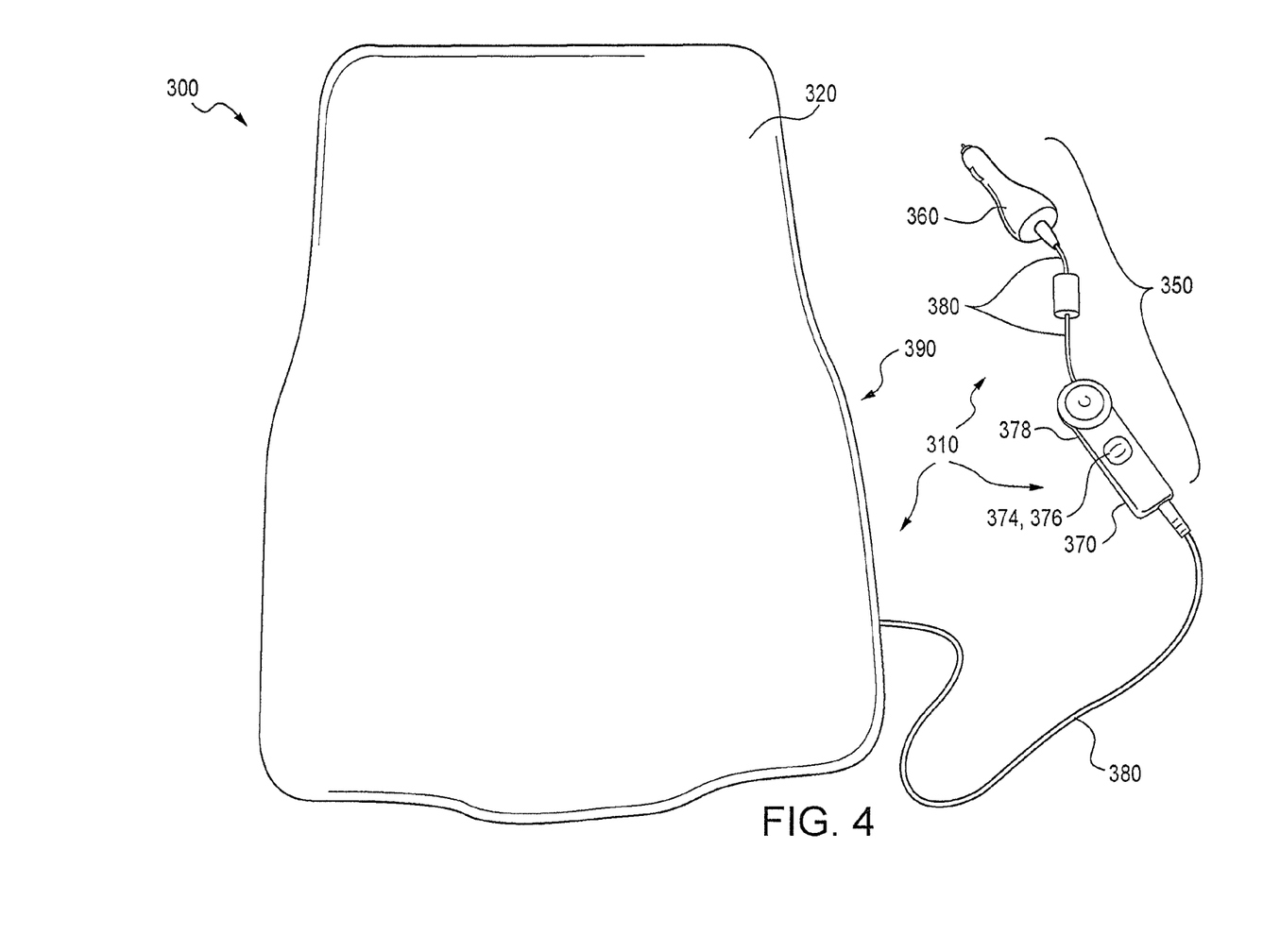
FIG. 4 is a schematic illustration of another preferred embodiment massaging foot mat in accordance with the present subject matter.

FIG. 4 illustrates another preferred embodiment massaging mat 300 in accordance with the present subject matter. The massaging mat 300 preferably comprises a mat 320 which depending upon the particular intended application, may be adapted for use as a floor mat in a vehicle cabin. The massaging mat 300 comprises a massage system 310. The massage system 310 is the same or similar as previously described massage systems 10, 110, and 210; with corresponding components using like reference numbers. Generally, the massage system 310 includes a control/power unit 350 which comprises a 12 VDC plug/adapter 360 and a control unit 370. The control unit 370 may include one or more control elements 374, one or more on/off elements 376 and a housing 378. A power/communication cord 380 extends between the control/power unit 350 and a massage module 390. The module 390 (not shown) is incorporated within the mat 320. The cord 380 or a portion thereof may also extend between the 12 VDC plug/adapter 360 and the control unit 370.

In particular versions of the present subject matter, the massage module or other vibration producing components, can be operated so as to provide a pulsating or intermittent mode of operation. Typically, therapeutic effects from vibratory massage modules can be realized at frequencies within a range of from about 10 to about 200 Hz. In a pulsating or intermittent mode of operation, periods of vibration are pulsed for actuation periods of from about 0.1 to about 5 seconds, with periods of nonactuation in which no vibrations are produced, of from about 0.1 to about 5 seconds. The time periods of each actuation period can be different or the same as other actuation periods. The time periods of each nonactuation period can be different or the same as other nonactuation periods. And, the time periods of the actuation period(s) can be different or the same as the nonactuation time periods. Generally, upon selection of a desired actuation and nonactuation time period for the massage module, the operation includes repetition of those time periods in a uniform and consistent manner until changed or discontinued by a user. Specifically, in this mode of operation, the massage module is repeatedly operated or actuated for a selected time period and is then de-activated for a selected time period, and this series of cycles is repeated. It will be appreciated that the present subject matter includes vibration frequencies, actuation periods, and nonactuation periods different than and/or outside of the ranges noted herein.

The present subject matter therapeutic mat or pad also may include one or more additional therapeutic components. A preferred example of such a component is an electrically operated resistive heating element. Thus, one or more heating elements could be incorporated in the massaging mats 100 and 300, or in the massaging seat system 200. The one or more resistive heating element(s) can be in nearly any shape, size, and/or configuration. However, it is preferred for most applications that the resistive heating element(s) be in the form of thin, flexible strips. The resistive heating elements are preferably permanently incorporated in the massaging foot mat or massaging seat system; however the subject matter includes versions in which the heating elements can be removed from the mat or system, such as for example to allow for replacement or washing of the mat or system. For versions in which the heating elements can be removed from a mat, it is contemplated that the heating elements can be accessed and/or removed either separately or collectively with the previously described massage modules.

In another aspect of the present subject matter, one or more vehicle mats are provided which include one or more vibratory components in combination with one or more illuminating elements and particular control provisions and operating modes. In this aspect, a user determines or selects (i) a desired operating mode for one or a plurality of mats, (ii) sets a desired operation of the vibratory component(s) which may be in the form of a massage module, and (iii) sets a desired operation of the one or more illuminating element(s).

Selection of a mat operating mode, i.e., (i), includes selecting whether a mat will operate in a single, stand alone mode or operate in a family mode (described in greater detail herein) and thus in association with one or more other mats in a family, e.g., a family of mats may constitute all or a portion of a plurality of mats in a vehicle.

Selecting operation of the vibratory component(s), i.e., (ii), includes selecting whether a vibratory component such as a massage module will operate continuously "on;" operate in a regular pulsed or intermittent fashion which typically includes selective adjustment of at least one of the time periods of each "on" duration, each "off" duration, or adjustment of both time periods; or operate in a random pulsed or intermittent fashion.

Selecting operation of the illuminating element(s), i.e., (iii), includes selecting whether one or more illuminating components such as a light incorporated in the mat and visible along an upwardly directed face of the mat operates so that the light is continuously "on;" operates in a pulsed or intermittent operation that is based upon the frequency of operational pulses of the vibratory components when those components are operated in a pulsed or intermittent fashion; or operates in a pulsed or intermittent operation that is based upon the frequency or pulses of other external factors such as noise or music within the vehicle. These aspects are described in greater detail herein.

As previously noted, in certain aspects of the present subject matter, a mat can also operate based upon the operation of another mat in a designated family of mats. Thus, when a mat is in "family" mode and when designated as a secondary mat, one or more of the components in the secondary mat can operate based upon information provided from a primary mat of the family. For example, for a family of four mats which may include a primary driver's side mat, a secondary passenger's side mat, and two secondary rear mats; the illuminating components of the three secondary mats can be configured to operate based upon information provided by the primary mat. For example, the lights of the three secondary mats (and optionally the lights of the primary mat) can be selected to operate by following the vibration mode selected for the primary mat. Alternatively, the lights of the three secondary mats (and optionally the lights of the primary mat) can be selected to operate based upon noise levels, and/or rhythm of music to which the mat(s) such as the primary mat is exposed. Thus, when in such a configuration, a family of mats can flash in unison and in conjunction with rhythm from music that is playing within a vehicle interior. These and other aspects are further described with reference to FIGS. 5 and 6.

Figure 5:
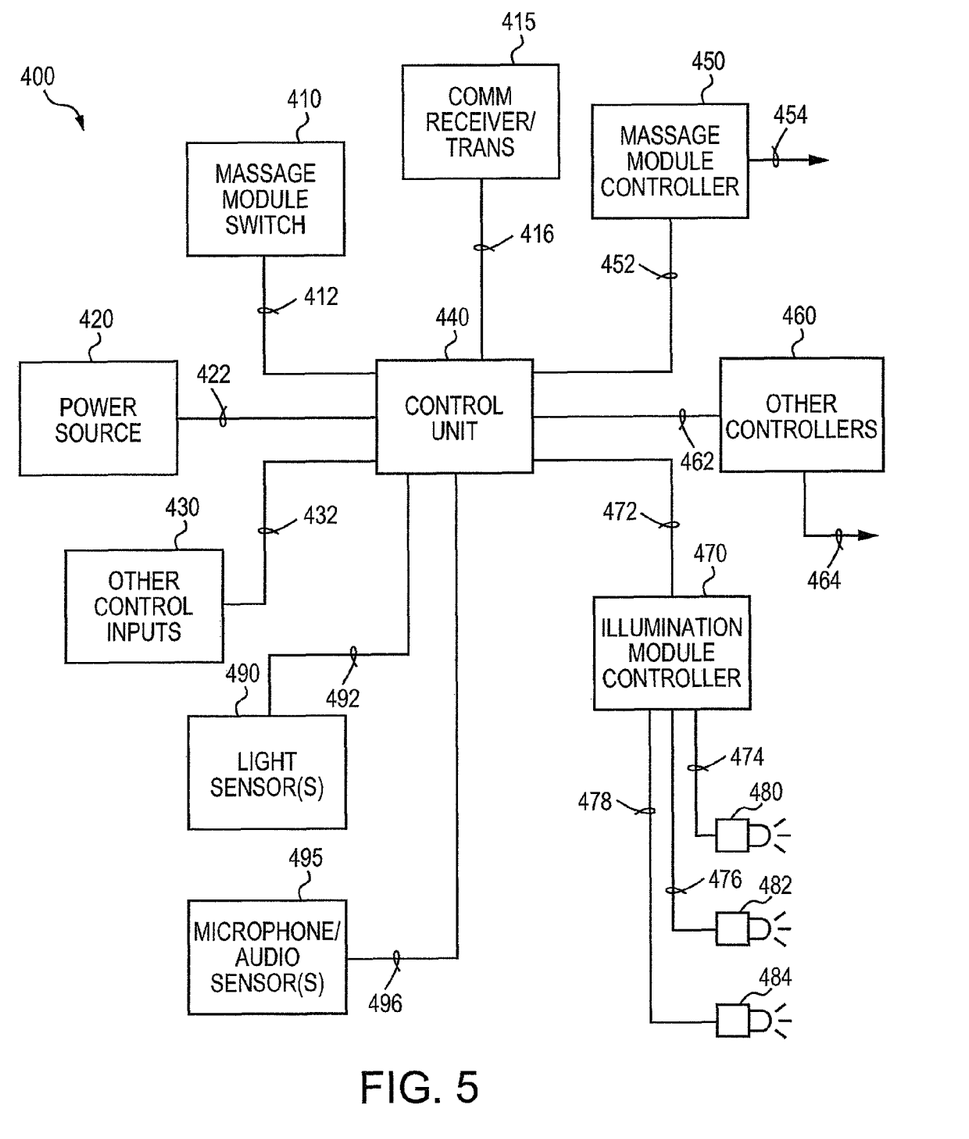
FIG. 5 is a schematic illustration of a vehicle mat system in accordance with another aspect of the present subject matter.

FIG. 5 is a schematic diagram of operational components in a vehicle mat system 400 of the present subject matter. The system 400 comprises a massage module switch 410 which can for example be provided in the form of an outwardly extending member such as the previously described bump 198. The system 400 also comprises one or more communication receiver(s) and/or transmitter(s) 415. These component(s) 415 are typically used when the mat is in a family mode of operation and the component(s) 415 provide information transfer or exchange between associated mats of a family. The communication receiver and/or transmitter(s) 415 can be in the form of BLUETOOTH receivers and transmitters as known in the art. BLUETOOTH communication components are known in the art, available commercially, and described in U.S. Pat. Nos. 7,844,224; 8,385,829; 7,292,823; 7,245,602; 6,650,549; 6,664,891; and 6,683,886. Other wireless formats are also contemplated. In certain versions of the present subject matter, it is also contemplated that a hardwired connection could be used to provide communication between associated mats. The system 400 also comprises a power source 420 such as one or more batteries that can be included in the mat or electrical connections to a vehicle's power source, and/or provisions for accessing or connecting to an external power source. In many versions of the present subject matter, the power source 420 is in the form of a 12 VDC male adapter plug, such as the previously described plug 360. The system 400 also comprises one or more other control inputs 430 which may be used to select or contribute in the operation of the system 400. The system also comprises a control unit 440 which is generally in the form of an electronic controller with memory and information or data processing capabilities. The system 400 additionally comprises one or more massage module controller(s) 450. The controller(s) 450 are configured to control and/or operate massage module(s) in a mat or other vibratory component(s) in a mat. The system 400 also optionally comprises one or more other controller(s) 460 for controlling and/or operating other components in the mat such as heaters for example. The system 400 additionally comprises one or more illumination module controller(s) 470. The illumination controller(s) 470 control operation of one or more illuminating elements such as lights 480, 482, and/or 484. It will be appreciated that the system 400 may include a lesser or greater number of lights than that depicted in FIG. 5. The system 400 may also comprise one or more light sensor(s) 490 and one or more microphone or audio or acoustic sensor(s) 495. The system 400 also includes one or more pathways for electrical power, grounding, and/or information or data transfer between components. For example, the system 400 can also comprise power and/or signal lines 412, 416, 422, 432, 452, 462, 472, 474, 476, 478, 492, and/or 496 as shown in FIG. 5.

All or a portion of these components and/or power and signal lines can be incorporated within a mat. In certain versions of the present subject matter, all components shown in FIG. 5 (excluding the optional components) except for the power source 420 can be included within and/or on a mat. A separable plug or cable connection could be provided for establishing electrical connection to a vehicle's power source. The optional components could be incorporated in the mat. It is also contemplated that the power source could be incorporated in the mat, for example in a thin battery pack.

In certain versions of the present subject matter, the mats may also include one or more light transmitting elements to transmit light emitted from one or more of the components 480, 482, and/or 484. The light transmitting elements can be in the form of optical fibers. The light transmitting elements may, if desired, be used to provide light emitted from a mat in a predetermined pattern, color, or combination of patterns and/or colors. A wide array of aesthetic designs and effects can be achieved by selective use of light transmitting elements in the mats. The light transmitting element(s) or component(s) can also be in the form of light tubes as known in the art. Light tubes are known in the art, commercially available, and described for example in U.S. Pat. No. 7,293,891.

A wide array of illuminating elements such as lights can be used in the present subject matter vehicle mats. Incandescent lamps can be used. Light emitting diodes (LED) are contemplated for use. Although white or blue-white light emitting elements can be used, the present subject matter includes the use of colored light emitters.

Figure 6:
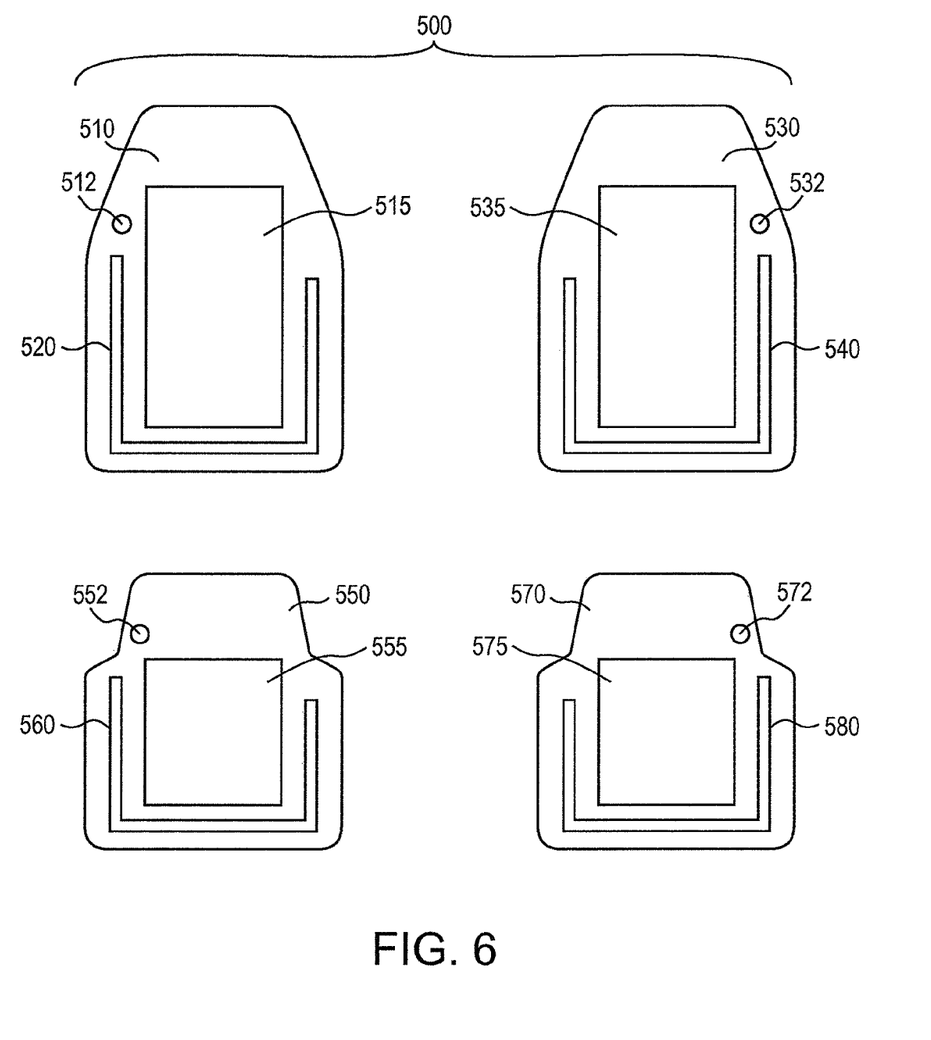
FIG. 6 is a schematic illustration of a plurality of vehicle mats in accordance with the present subject matter.

FIG. 6 schematically illustrates a plurality 500 of vehicle mats and in particular, a set or family of vehicle mats. The plurality 500 of mats comprise a front driver's side mat 510, a front passenger's side mat 530, and two rear mats 550 and 570. The rear mats may include a driver's side rear mat and a passenger's side rear mat. In many versions of the present subject matter, each mat includes a control switch, one or more massage modules, and one or more illuminating elements. For example, the mat 510 includes a control switch 512, a massage module 515, and a light 520; the mat 530 includes a control switch 532, a massage module 535, and a light 540; the mat 550 includes a control switch 552, a massage module 555, and a light 560; and the mat 570 includes a control switch 572, a massage module 575, and a light 580. Each mat, a portion of the mats, or all of the mats can include any of the components and/or optional features such as a heating element.

As previously noted, each mat 510, 530, 550, and 570 can be operated in a single, stand-alone mode or in a family mode. The construction or structure of each of the mats of a family may be the same or different from one another. In many embodiments, one or more of the secondary mats, e.g. a passenger side front mat, a driver's side rear mat, and a passenger's side rear mat, utilize the same or substantially the same construction as the primary mat, e.g. a driver's side front mat. In addition, one or more or all of the secondary vehicle floor mats can also utilize and/or contain the same components and same configuration of components as the primary mat of a family of mats.

It will be understood that the present subject matter includes families of mats and their operation which include a lesser or greater number of mats than those depicted in FIG. 6. It is also contemplated that a single family of mats may include mats in multiple vehicles and/or mats which are separated from one another by relatively significant distances. For example, the present subject matter includes collections of mats in multiple vehicles such as at vehicle gatherings, shows, or other events or displays.

As previously noted, in certain aspects of the present subject matter, the mats can be configured such that during their operation, the operation of the illuminating element(s) or lights of a mat is dependent upon the operation of the vibratory component(s) or massage module. Specifically, for example if the massage module is set to operate in an intermittent fashion such as with intermittent time periods of 0.5 seconds "on" and 0.5 seconds "off," operation of the light(s) can be set so the lights also flash at the same or substantially the same intermittent pattern of on and off pulses. The lights in such mode, are referred to herein as "following" the operation of the massage module. The lights can also be configured to follow a continuously on operation of the massage module.

In addition and as previously noted, in certain aspects of the present subject matter, the mats can be configured such that during their operation, the operation of the illuminating element(s) or lights of a mat is dependent upon the level or change in acoustic levels within the interior of the vehicle for example. In this mode of operation, an acoustic sensor such as sensor 495 and/or the control unit 440 in FIG. 5 senses changes in audio parameters such as acoustic frequency, amplitude, or other factors and provides a control output signal that is proportional to or which "follows" the rhythm or beat of music for example. That control output signal for example schematically shown in FIG. 5 as 472, is used to control the operation of the illuminating elements such as lights 480, 482, and/or 484 in the mat.

In a particular version of the present subject matter, a single mat and/or a family of mats can be configured to operate or change or modify their operation based upon voice commands from a user. For example, the mat(s) could include voice recognition technology and processing provisions incorporated in the control unit 440 of FIG. 5. Thus, upon sensing issuance of a voice command or verbal instructions from a user for example a driver, by the audio sensor 495, the control unit 440 determines an appropriate response such as generating or modifying a control output signal 474, 476, and/or 478 to the illuminating elements 480, 482, and/or 484. The control unit 440 could also be configured to operate or change operation of the massage module and/or other component(s) based upon verbal commands from a user.

Yet another aspect of the present subject matter is the provision of an audio output component such as an audio speaker that is incorporated in the mat(s). Referring to FIG. 5, the controller 460 could be utilized to drive an audio speaker incorporated in a mat based upon a control signal from the control unit and processing provisions 440. The mat and associated components and/or circuitry could be configured to provide audio outputs via the speaker which might provide confirmation of mat operation, or changes in mat operating mode. It is also contemplated that the mat could be configured to provide greetings to a user or occupant(s) of a vehicle for example.

Voice or speech recognition technologies and speech synthesis technologies are known in the art, commercially available, and described in a number of patents such as for example U.S. Pat. Nos. 7,174,299; 8,401,847; 6,834,265; 7,174,298; 7,280,969; 8,055,501; and 7,143,038.

In still another version of the present subject matter, the mat(s) can utilize integrated motion sensing provisions. The motion sensing provisions could for example detect actual motion of the mat(s) such as when in a moving vehicle. Such sensing could be accomplished for example by GPS technology which in turn could also be incorporated in the mat(s) or other components which the mat(s) could be configured to communicate with such as a user's phone, a separate vehicular GPS system, or the like. The motion sensing provisions could alternatively detect changes in acceleration which would signify that the vehicle containing the mats was in motion. One or more accelerometers and associated circuitry could be incorporated in the mat(s).

Mat(s) including motion sensing provisions can be configured to adjust or terminate operation of blinking or flashing lights based upon the detection of motion of the vehicle. Such configuration may be beneficial with regard to safety concerns when a driver is operating a vehicle. For example, if a mat is in a mode in which lights of the mat are flashing, upon sensing motion of the vehicle, the flashing could be discontinued or the intensity or brightness of the lights could be reduced. Other operational changes could also be initiated by the motion sensing provisions.

It is also contemplated that the motion sensing provisions could be configured to alter the operation of the massage module and/or other components of the mat. For example, upon sensing vehicle motion, the mat may be configured to activate the massage module and/or heating element. A wide array of operational configurations are contemplated by the present subject matter.

The preferred embodiment mats can be formed using constructions, materials, and components described in the prior art, such as for example in one or more of U.S. Pat. Nos. 2,476,921; 3,100,483; 4,326,506; 4,329,981; 5,254,384; 5,490,821; 5,628,079; 6,579,250; and 7,297,126. In addition, various vibration-providing components and heating systems are known in the art, commercially available, and potentially eligible for use in the preferred embodiment mats described herein. For example, flexible heating elements and controllers are available from Birk Manufacturing of East Lyme, Conn.; and Watlow of St. Louis, Mo.

Although the present subject matter has been described in terms of a floor mat and a seating system; it will be understood that the present subject matter can be provided in numerous other forms and configurations. Furthermore, although the floor mats and seating systems are primarily described in terms of application within a vehicle cabin or interior, it will be appreciated that the present subject matter is not limited to such applications.

In certain versions of the present subject matter, the mats are particularly adapted for use with and placement within a vehicle such as an automobile. Accordingly, in such versions, the mats may include one or more fixation points or components that are configured to correspond to fixation points located on a vehicle floor. For example, a mat may be provided with one or more apertures that are located at particular locations on the mat. The apertures are located such that when the mat is positioned on a floor region of a vehicle, such as on a driver's side region, a corresponding upwardly projecting member can extend at least partially within or through the opening. Releasably engaging snap members or other assemblies are also contemplated for the fixation points.

Although vehicular components and systems are known which utilize speech recognition systems and/or speech synthesis technologies, such systems are incorporated or integral with the vehicle. The present subject matter mats or families of mats if provided with the noted speech recognition and/or speech synthesis systems, can be used in a number of different vehicles. Moreover, a user can easily remove a mat or family of mats from one vehicle and place the mat(s) in a different vehicle if desired.

Many other benefits will no doubt become apparent from future application and development of this technology.

All patents, published applications, and articles noted herein are hereby incorporated by reference in their entirety.

As described hereinabove, the present subject matter solves many problems associated with previous type devices. However, it will be appreciated that various changes in the details, materials and arrangements of parts, which have been herein described and illustrated in order to explain the nature of the subject matter, may be made by those skilled in the art without departing from the principle and scope of the subject matter, as expressed in the appended claims.

What is claimed is:

1. A vehicle floor mat, the mat comprising:
 a thin, planar, flexible member defining an upwardly directed first face, an oppositely directed second face, and an interior hollow region between at least a portion of the first face and the second face, the flexible member sized and shaped to reside along the floor of a vehicle cabin;
 a massage module removably disposed in the interior hollow region of the flexible member, the massage module emitting vibratory motion upon application of electrical power to the massage module;
 at least one illuminating element affixed to the flexible member and visible along the first face of the flexible member upon application of electrical power to the illuminating element;
 control provisions;
 wherein the control provisions are configured to control the operation of the massage module and the at least one illuminating element, such that the operation of the illuminating element is dependent upon and follows the operation of the massage module.

2. The vehicle floor mat of claim 1, wherein the massage module is configured to operate in a pulsating mode with an actuation time period in a range of from 0.1 seconds to 5 seconds, and a nonactuation time period of from 0.1 seconds to 5 seconds, the at least one illuminating element thus also operating with an actuation time period and a nonactuation time period which are substantially the same as those of the massage module.

3. The vehicle floor mat of claim 1, further comprising:
 at least one fixation component adapted to engage with a corresponding other fixation component disposed along a vehicle floor.

4. The vehicle floor mat of claim 1, further comprising:
 at least one light transmission component incorporated within the mat.

5. The vehicle floor mat of claim 4, wherein the light transmission component is selected from the group consisting of an optical fiber, a light tube, and combinations thereof.

6. The vehicle floor mat of claim 1, further comprising:
 at least one component selected from the group consisting of (i) at least one light sensor, (ii) at least one acoustic sensor, (iii) provisions for generating an audible output, (iv) provisions for providing wireless communication of the mat with another component, (v) a heating element emitting heat upon application of electrical power to the heating element, and (vi) combinations of (i)-(v).

7. A vehicle floor mat, the mat comprising:
 a thin, planar, flexible member defining an upwardly directed first face, an oppositely directed second face, and an interior hollow region between at least a portion of the first face and the second face, the flexible member sized and shaped to reside along the floor of a vehicle cabin;
 a massage module removably disposed in the interior hollow region of the flexible member, the massage module emitting vibratory motion upon application of electrical power to the massage module;
 at least one illuminating element affixed to the flexible member and visible along the first face of the flexible member upon application of electrical power to the illuminating element;
 an acoustic sensor and control provisions incorporated in the mat and configured to provide a control output signal based upon acoustic parameters sensed by the acoustic sensor;

wherein the control provisions are configured to control the operation of the at least one illuminating element based at least in part upon the control output signal, such that the operation of the illuminating element is dependent upon and follows the acoustic parameters in the vehicle.

8. The vehicle floor mat of claim 7, further comprising:
at least one fixation component adapted to engage with a corresponding other fixation component disposed along a vehicle floor.

9. The vehicle floor mat of claim 7, further comprising:
at least one light transmission component incorporated within the mat.

10. The vehicle floor mat of claim 9, wherein the light transmission component is selected from the group consisting of an optical fiber, a light tube, and combinations thereof.

11. The vehicle floor mat of claim 7, further comprising:
at least one component selected from the group consisting of (i) at least one light sensor, (ii) provisions for generating an audible output, (iii) provisions for providing wireless communication of the mat with another component, (iv) a heating element emitting heat upon application of electrical power to the heating element, and (v) combinations of (i)-(iv).

12. A plurality of vehicle floor mats comprising:
a primary vehicle floor mat including (i) at least one illuminating element, (ii) at least one vibratory component, and (iii) control provisions for controlling operation of the at least one illuminating element and the at least one vibratory component;
at least one secondary vehicle floor mat, each secondary vehicle floor mat comprising (i) at least one illuminating element, and (ii) at least one vibratory component, wherein operation of the at least one illuminating element of the secondary vehicle floor mat and the at least one vibratory component of the secondary vehicle floor mat are controlled by the control provisions of the primary vehicle floor mat.

13. The plurality of vehicle floor mats of claim 12, wherein the operation of the at least one vibratory component of the secondary vehicle floor mat and the at least one illuminating element of the secondary vehicle floor mat follow the operation of the vibratory component of the primary vehicle floor mat.

14. The plurality of vehicle floor mats of claim 12, the primary vehicle floor mat further including an acoustic sensor, wherein the control provisions of the primary vehicle floor mat are configured to provide a control output signal based upon acoustic parameters sensed by the acoustic sensor, wherein the control provisions of the primary vehicle floor mat are configured to control the operation of the at least one illuminating element of the primary vehicle floor mat based at least in part upon the control output signal, such that the operation of the at least one illuminating element of the primary vehicle floor mat is dependent upon and follows acoustic parameters in the vehicle.

15. The plurality of vehicle floor mats of claim 14, wherein the illuminating elements of the at least one secondary vehicle floor mat are configured to operate at least in part based upon the control output signal of the primary vehicle floor mat.

16. The plurality of vehicle floor mats of claim 12, wherein the at least one secondary vehicle floor mat includes (i) a passenger's front side floor mat, (ii) a driver's side rear floor mat, and (iii) a passenger's side rear floor mat.

17. The plurality of vehicle floor mats of claim 12, wherein the primary vehicle floor mat and each secondary vehicle floor mat further includes provisions for providing wireless communication between the primary vehicle floor mat and the secondary vehicle floor mats.

18. The plurality of vehicle floor mats of claim 12, wherein (i) the primary vehicle floor mat is a thin, planar, flexible member defining an upwardly directed first face, an oppositely directed second face, and an interior hollow region between at least a portion of the first face and the second face, (ii) at least one vibratory component of the primary vehicle floor mat is a massage module that is removably disposed in the interior hollow region of the primary vehicle floor mat, the massage module emitting vibratory motion upon application of electrical power to the massage module, (iii) the at least one illuminating element of the primary vehicle floor mat is visible along the first face of the flexible member upon application of electrical power to the illuminating element, (iv) the secondary vehicle floor mat is a thin, planar, flexible member defining an upwardly directed first face, an oppositely directed second face, and an interior hollow region between at least a portion of the first face and the second face, (v) at least one vibratory component of the secondary vehicle floor mat is a massage module that is removably disposed in the interior hollow region of the secondary vehicle floor mat, the massage module emitting vibratory motion upon application of electrical power to the massage module, and (vi) the at least one illuminating element of the secondary vehicle floor mat is visible along the first face of the flexible member upon application of electrical power to the illuminating element.

* * * * *